(12) United States Patent
Lee et al.

(10) Patent No.: US 8,809,597 B2
(45) Date of Patent: Aug. 19, 2014

(54) SEPARATION OF VAPOR CRUDE ALCOHOL PRODUCT

(75) Inventors: David Lee, Seabrook, TX (US); Adam Orosco, Houston, TX (US); Lincoln Sarager, Houston, TX (US); Trinity Horton, Houston, TX (US); Radmila Jevtic, Pasadena, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 460 days.

(21) Appl. No.: 13/094,450

(22) Filed: Apr. 26, 2011

(65) Prior Publication Data

US 2012/0010436 A1   Jan. 12, 2012

Related U.S. Application Data

(60) Provisional application No. 61/363,089, filed on Jul. 9, 2010.

(51) Int. Cl.
*C07C 29/80* (2006.01)
*C07C 29/76* (2006.01)

(52) U.S. Cl.
CPC .............. *C07C 29/80* (2013.01); *C07C 29/76* (2013.01)
USPC ............ 568/885; 568/916; 568/917; 568/918

(58) Field of Classification Search
CPC ........ C07C 29/76; C07C 29/80; C07C 29/82; C07C 29/84
USPC .................................. 568/885, 916, 917, 918
See application file for complete search history.

(56) References Cited

U.S. PATENT DOCUMENTS

| | | |
|---|---|---|
| 2,649,407 A | 8/1953 | Harrison |
| 2,702,783 A | 2/1955 | Harrison |
| 2,801,209 A | 7/1957 | Muller |
| 2,882,244 A | 4/1959 | Milton |
| 3,130,007 A | 4/1964 | Breck |
| 3,408,267 A | 10/1968 | Miller |
| 3,445,345 A | 5/1969 | Adam |
| 3,478,112 A | 11/1969 | Adam |

(Continued)

FOREIGN PATENT DOCUMENTS

| | | |
|---|---|---|
| EP | 0104197 | 4/1984 |
| EP | 0167300 | 1/1986 |

(Continued)

OTHER PUBLICATIONS

International Written Opinion mailed Jul. 10, 2012 in corresponding International Application No. PCT/US2011/042755.

(Continued)

*Primary Examiner* — Rosalynd Keys

(57) ABSTRACT

Recovery of alcohol, in particular ethanol, by separating a vapor crude alcohol product obtained from the hydrogenation of acetic acid using a low energy process. The vapor crude ethanol product is separated in a column to produce a distillate stream comprising ethanol and at least one non-condensable gas. The vapor crude ethanol product may pass through a membrane before the first distillation column to separate the at least one non-condensable gas from the ethanol. The ethanol product is subsequently recovered from the distillate stream.

18 Claims, 2 Drawing Sheets

(56) References Cited

U.S. PATENT DOCUMENTS

| | | |
|---|---|---|
| 3,990,952 A | 11/1976 | Katzen |
| 4,275,228 A | 6/1981 | Gruffaz |
| 4,306,942 A | 12/1981 | Brush |
| 4,317,918 A | 3/1982 | Takano |
| 4,319,058 A | 3/1982 | Kulprathipanja |
| 4,379,028 A | 4/1983 | Berg |
| 4,395,576 A | 7/1983 | Kwantes |
| 4,398,039 A | 8/1983 | Pesa |
| 4,421,939 A | 12/1983 | Kiff |
| 4,422,903 A | 12/1983 | Messick |
| 4,454,358 A | 6/1984 | Kummer |
| 4,465,854 A | 8/1984 | Pond |
| 4,471,136 A | 9/1984 | Larkins |
| 4,480,115 A | 10/1984 | McGinnis |
| 4,492,808 A | 1/1985 | Hagen |
| 4,497,967 A | 2/1985 | Wan |
| 4,520,213 A | 5/1985 | Victor |
| 4,541,897 A | 9/1985 | Sommer |
| 4,626,321 A | 12/1986 | Grethlein |
| 4,678,543 A | 7/1987 | Houben |
| 4,692,218 A | 9/1987 | Houben |
| 4,777,303 A | 10/1988 | Kitson |
| 4,804,791 A | 2/1989 | Kitson |
| 4,842,693 A | 6/1989 | Wheldon |
| 4,961,826 A | 10/1990 | Grethlein |
| 4,985,572 A | 1/1991 | Kitson |
| 4,990,655 A | 2/1991 | Kitson |
| 4,994,608 A | 2/1991 | Torrence |
| 5,001,259 A | 3/1991 | Smith |
| 5,026,908 A | 6/1991 | Smith |
| 5,035,776 A | 7/1991 | Knapp |
| 5,061,671 A | 10/1991 | Kitson |
| 5,124,004 A | 6/1992 | Grethlein |
| 5,144,068 A | 9/1992 | Smith |
| 5,149,680 A | 9/1992 | Kitson |
| 5,185,481 A | 2/1993 | Muto |
| 5,215,902 A | 6/1993 | Tedder |
| 5,227,141 A | 7/1993 | Kim |
| 5,233,099 A | 8/1993 | Tabata |
| 5,237,108 A | 8/1993 | Marraccini |
| 5,250,271 A | 10/1993 | Horizoe |
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli |
| RE35,377 E | 11/1996 | Steinberg |
| 5,599,976 A | 2/1997 | Scates |
| 5,762,765 A | 6/1998 | Berg |
| 5,770,770 A | 6/1998 | Kim |
| 5,800,681 A | 9/1998 | Berg |
| 5,821,111 A | 10/1998 | Grady |
| 5,993,610 A | 11/1999 | Berg |
| 6,121,498 A | 9/2000 | Tustin |
| 6,143,930 A | 11/2000 | Singh |
| 6,232,352 B1 | 5/2001 | Vidalin |
| 6,294,703 B1 | 9/2001 | Hara |
| 6,375,807 B1 | 4/2002 | Nieuwoudt |
| 6,509,180 B1 | 1/2003 | Verser |
| 6,627,770 B1 | 9/2003 | Cheung |
| 6,657,078 B2 | 12/2003 | Scates |
| 6,685,754 B2 | 2/2004 | Kindig |
| 6,693,213 B1 | 2/2004 | Kolena |
| 6,723,886 B2 | 4/2004 | Allison |
| 6,755,975 B2 * | 6/2004 | Vane et al. .................... 210/640 |
| 6,906,228 B2 | 6/2005 | Fischer |
| 6,927,048 B2 | 8/2005 | Verser |
| 7,005,541 B2 | 2/2006 | Cheung |
| 7,074,603 B2 | 7/2006 | Verser |
| 7,115,772 B2 | 10/2006 | Picard |
| 7,208,624 B2 | 4/2007 | Scates |
| 7,297,236 B1 | 11/2007 | Vander Griend |
| 7,351,559 B2 | 4/2008 | Verser |
| 7,399,892 B2 | 7/2008 | Rix |
| 7,507,562 B2 | 3/2009 | Verser |
| 7,553,397 B1 | 6/2009 | Colley |
| 7,572,353 B1 | 8/2009 | Vander Griend |
| 7,601,865 B2 | 10/2009 | Verser |
| 7,608,744 B1 | 10/2009 | Johnston |
| 7,682,812 B2 | 3/2010 | Verser |
| 7,732,173 B2 | 6/2010 | Mairal |
| 7,744,727 B2 | 6/2010 | Blum |
| 7,863,489 B2 | 1/2011 | Johnston |
| 7,884,253 B2 | 2/2011 | Stites |
| 7,888,082 B2 | 2/2011 | Verser |
| 2006/0019360 A1 | 1/2006 | Verser |
| 2006/0127999 A1 | 6/2006 | Verser |
| 2007/0144886 A1 | 6/2007 | Sylvester |
| 2007/0270511 A1 | 11/2007 | Melnichuk |
| 2008/0135396 A1 | 6/2008 | Blum |
| 2008/0193989 A1 | 8/2008 | Verser |
| 2009/0014313 A1 | 1/2009 | Lee |
| 2009/0023192 A1 | 1/2009 | Verser |
| 2009/0069609 A1 | 3/2009 | Kharas |
| 2009/0081749 A1 | 3/2009 | Verser |
| 2009/0166172 A1 | 7/2009 | Casey |
| 2009/0281354 A1 | 11/2009 | Mariansky |
| 2009/0318573 A1 | 12/2009 | Stites |
| 2010/0029980 A1 | 2/2010 | Johnston |
| 2010/0029995 A1 | 2/2010 | Johnston |
| 2010/0030001 A1 | 2/2010 | Chen |
| 2010/0030002 A1 | 2/2010 | Johnston |
| 2010/0121114 A1 | 5/2010 | Weiner |
| 2010/0197485 A1 | 8/2010 | Johnston |
| 2012/0010437 A1 | 1/2012 | Jevtic |
| 2012/0010438 A1 | 1/2012 | Lee |
| 2012/0010439 A1 | 1/2012 | Jevtic |
| 2012/0010440 A1 | 1/2012 | Sarager |
| 2012/0273338 A1 | 11/2012 | Lee |
| 2012/0277481 A1 | 11/2012 | Warner |

FOREIGN PATENT DOCUMENTS

| | | |
|---|---|---|
| EP | 0456647 | 7/1990 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4193304 | 7/1992 |
| WO | 8303409 | 10/1983 |
| WO | 2008135192 | 11/2008 |
| WO | 2009009322 | 1/2009 |
| WO | 2009009323 | 1/2009 |
| WO | 2009048335 | 4/2009 |
| WO | 2009063176 | 5/2009 |
| WO | 2010055285 | 5/2010 |

OTHER PUBLICATIONS

International Preliminary Report on Patentability mailed Sep. 28, 2012 in corresponding International Application No. PCT/US2011/042755.

Alcala, et al., (2005). Experimental and DFT studies of the conversion of ethanol and acetic acid on PtSn-based catalysts, Journal of Physical Chemistry, 109(6), 2074-2085.

Amit M. Goda et al., DFT modeling of selective reduction of acetic acid to acetaldehyde on Pt-based bimetallic catalysts, 20th NAM, Houston, TX, Jun. 17-22, 2007 available online at http://www.nacatsoc.org/20nam/abstracts/O-S9-18.pdf.

Burkhanov, et al., "Palladium-Based Alloy Membranes for Separation of High Purity Hydrogen from Hydrogen-Containing Gas Mixtures," Platinum Metals Rev., 2011, 55, (1), pp. 3-12.

English language abstarct for JP 4193304 A, Jul. 1992.

English language abstract for EP 0 456 647 A1, Jul. 1990.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Hilmen, Separation of Azeotropic Mixtures: Tools for Analysis and Studies on Batch Distillation Operation (Nov. 2000) p. 17-20.

(56) References Cited

OTHER PUBLICATIONS

International Search Report and Written Opinion for PCT/US2011/042755 mailed Jan. 23, 2012.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Rachmady, Acetic Acid Reduction by H2 on Bimetallic Pt" Fe Catalysts, Journal of Catalysis 209, 87-98 (Apr. 1, 2002), Elsevier Science (USA).

Santori et al. (2000). Hydrogenation of carbonylic compounds on Pt/SiO2 catalysts modified with SnBu4, Studies in Surface Science and Catalysis, 130, 2063-2068.

ZeaChem, Inc., Technology Overview, Lakewood, Colorado www.zeachem.com, 2008.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

Response to Final Office Action for U.S. Appl. No. 13/094,488, filed Oct. 18, 2013.

Response to Final Office Action for U.S. Appl. No. 13/094,610, filed Oct. 18, 2013.

Response to Final Office Action for U.S. Appl. No. 13/094,688, filed Nov. 25, 2013.

Response to Final Office Action for U.S. Appl. No. 13/094,661, filed Nov. 25, 2013.

* cited by examiner

SEPARATION OF VAPOR CRUDE ALCOHOL PRODUCT

CROSS REFERENCE TO RELATED APPLICATIONS

This application claims priority to U.S. Provisional App. No. 61/363,089, filed on Jul. 9, 2010, the entirety of which is incorporated herein by reference.

FIELD OF THE INVENTION

The present invention relates generally to processes for producing alcohol and, in particular, to process for recovering ethanol by feeding a vapor crude ethanol product to a distillation column.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition, when conversion is incomplete, unreacted acetic acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising hydrogenating acetic acid from an acetic acid feed stream in a reactor to produce a vapor crude ethanol product; separating at least a portion of the vapor crude ethanol product in a first distillation column to produce a first residue comprising acetic acid and a first distillate comprising ethanol and at least one non-condensable gas; and recovering ethanol from the first distillate.

In a second embodiment, the present invention is directed to a process for producing ethanol, comprising providing a vapor crude ethanol product comprising ethanol, acetic acid, water, ethyl acetate, and at least one non-condensable gas; separating at least a portion of the vapor crude ethanol product in a first distillation column into a first residue comprising acetic acid and a first distillate comprising ethanol and the at least one non-condensable gas; separating at least a portion of the first distillate to yield a vapor stream comprising the at least one non-condensable gas and a liquid stream comprising ethanol; and recovering ethanol from the liquid stream.

In a third embodiment, the present invention is directed to a process for producing ethanol, comprising hydrogenating acetic acid from an acetic acid feed stream in a reactor to produce a vapor crude ethanol product; separating at least a portion of the vapor crude ethanol product in a first membrane to produce a first permeate comprising at least one non-condensable gas, and a first retentate comprising acetic acid, ethanol, ethyl acetate and water; and recovering ethanol from the first retentate.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
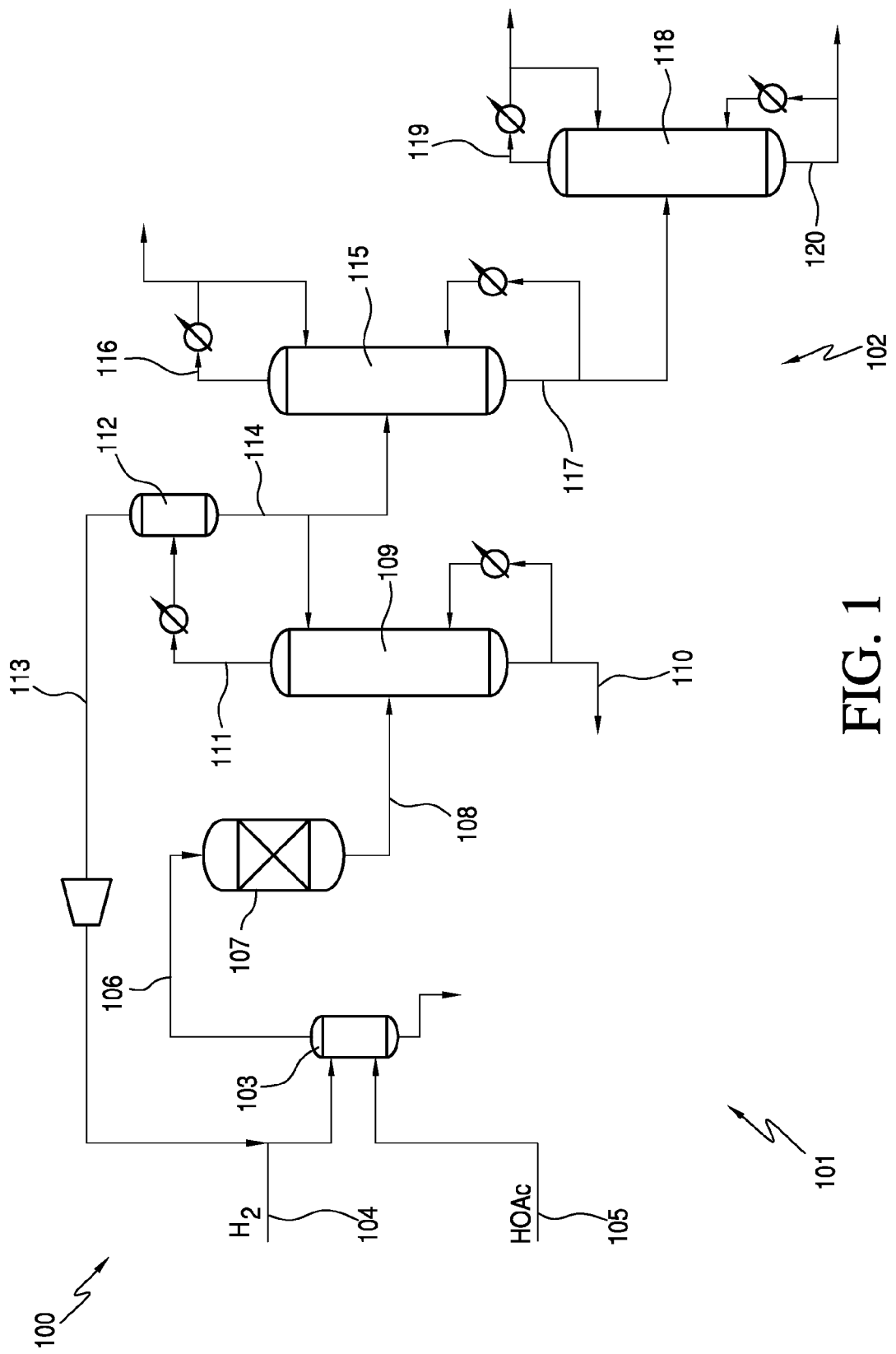
FIG. 1 is a schematic diagram of an ethanol production system in accordance with one embodiment of the present invention.

The catalytic hydrogenation of acetic acid according the invention produces a crude alcohol product, e.g. a crude ethanol product that comprises ethanol, water, ethyl acetate, acetic acid, non-condense able gases, and other impurities. The hydrogenation reaction is typically conducted in the vapor phase and yields a crude ethanol product that is in the vapor phase. The present invention relates to processes for recovering ethanol from this vapor crude ethanol product, without condensing the crude ethanol product.

The crude ethanol product possesses a sufficient heat quantity to drive separation in the initial distillation column. For example, the reaction temperature is typically greater than the temperature required at the base of the initial separation column. This may allow for direct heat integration such that the heat of reaction contained in the vapor crude ethanol product may be used in the initial separation column to drive the separation process. This direct heat exchange offers an opportunity to reduce the energy supplied to the column reboiler and thus reduce the size and capital required for the reboiler. Feeding a vapor feed stream to the column may reduce the reboiler load because the latent heat of vaporization is provided from the feed.

The crude ethanol product may also comprise one or more non-condensable gases selected from the group consisting of hydrogen, carbon monoxide, carbon dioxide, methane, ethane, and mixtures thereof. Depending on the concentration of these gases, in particular hydrogen, it may be difficult to maintain a vapor liquid equilibrium in the initial separation column, i.e., distillation column. Thus, preferably one or more of these non-condensable gases, in particular hydrogen, may be removed from the vapor crude ethanol product without condensing. In one embodiment, a hydrogen permeate membrane may be used to maintain the vapor state of the remaining crude ethanol product. Hydrogen may be removed as the permeate, while the remaining crude ethanol product forms the retentate. In this aspect of the invention, the retentate remains in the vapor phase and may be fed directly to the initial separation column. Any remaining non-condensable gases in the retentate may be withdrawn by partially condensing the distillate of the initial separation column. The low-boiling organic components and any remaining trace hydrogen may be separated and vented from the bulk of the organic liquid in this partial condenser. Ethanol may be recovered from the condensed distillate.

The hydrogen membrane may be a polymer based membrane operate at a maximum temperature of 100° C. and at a pressure of greater than 500 kPa, e.g., greater than 700 kPa. In another embodiment, the hydrogen membrane is a palladium-based membrane, such as palladium-based alloy with copper, yttrium, ruthenium, indium, lead, and/or rare earth metals, that has a high selectivity for hydrogen. Suitable palladium-based membranes are described in Burkhanov, et al., "Palladium-Based Alloy Membranes for Separation of High Purity Hydrogen from Hydrogen-Containing Gas Mixtures," *Platinum Metals Rev.*, 2011, 55, (1), 3-12, the entirety of which is incorporated by reference. Efficient hydrogen separation palladium-based membranes generally have high hydrogen permeability, low expansion when saturated with hydrogen, good corrosion resistance and high plasticity and strength during operation at temperatures of 100° C. to 900° C., e.g., from 300° C. to 700° C. Because the crude ethanol product may contain unreacted acetic acid, the hydrogen membrane should tolerate acidic conditions of about pH 1.

In another embodiment, the vapor crude ethanol product from the reactor may be directly fed to the initial separation column, without an initial hydrogen separation. Depending on the operation conditions of the initial separation column and the composition of crude ethanol product, the initial separation column may withdraw a majority of the acetic acid from the vapor crude ethanol product in the residue. In some embodiments, water may also be withdrawn in the residue. The distillate from the separation column may be condensed and fed to an overhead flasher or knock-out pot. Non-condensable gases such as hydrogen are separated in a vapor phase from the flasher, and may be purged from the system or returned to the reactor. The liquid phase from the flasher is preferably separated into two portions. A first portion of the liquid phase is preferably refluxed to the initial separation column, and a second portion of the liquid phase is further separated to recover ethanol.

Hydrogenation of Acetic Acid

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include siliceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $CO_2O_3$, or $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain Nor Pro. The Saint-Gobain Nor Pro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g H$_2$O/g support, a surface area of about 160 to 175 m$^2$/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, carbon dioxide, carbon monoxide, and mixtures thereof. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. For purposes of clarity, the concentrations of non-condensable gases, e.g., hydrogen, carbon monoxide, and carbon dioxide, are not shown in Table 1. The hydrogen concentrations will vary depending on the molar feed ratios. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Ethanol Recovery Systems

Figure 2:
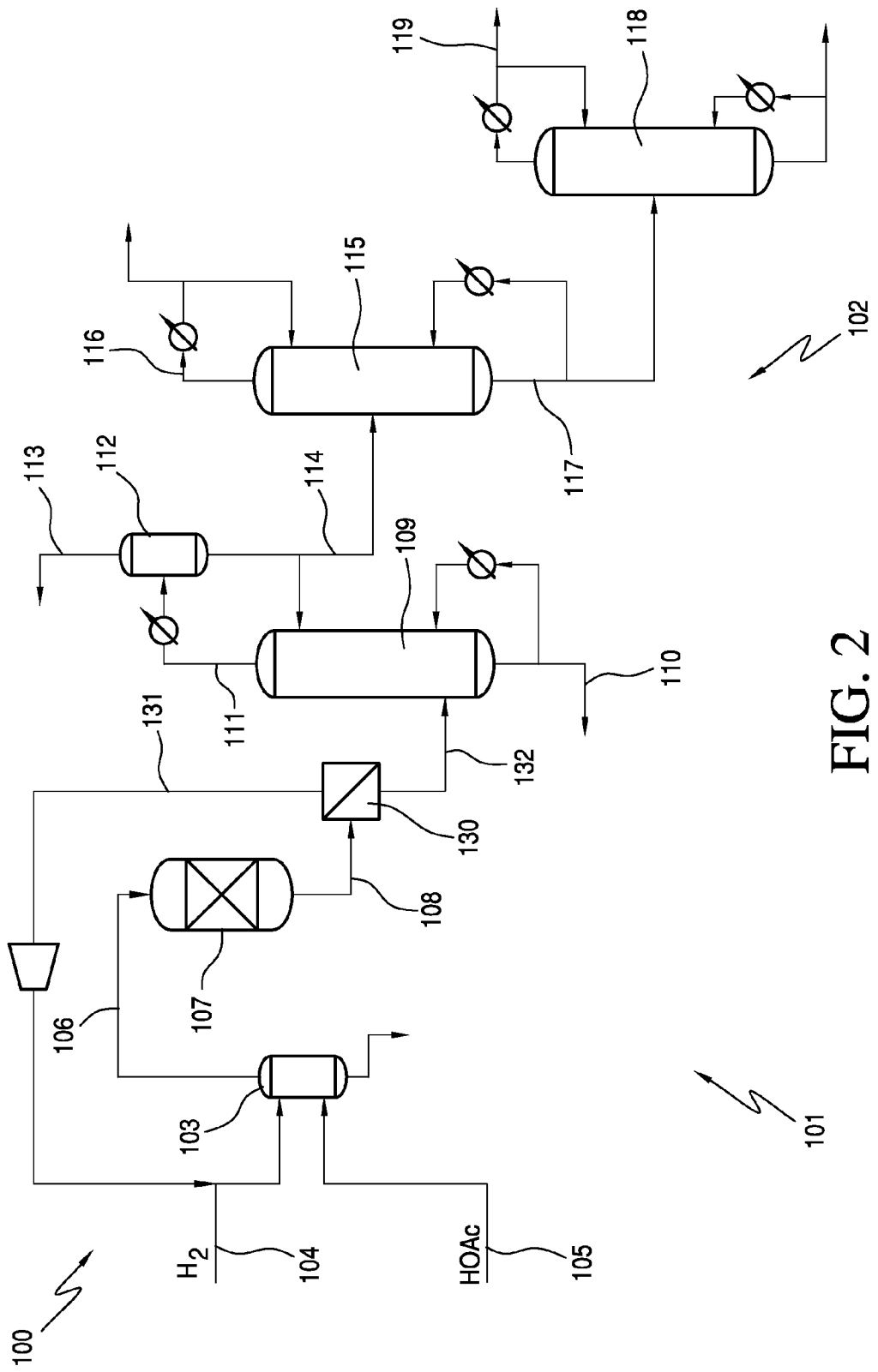
FIG. 2 is a schematic diagram of an ethanol production system having a hydrogen membrane in accordance with one embodiment of the present invention.

Exemplary ethanol recovery systems in accordance with embodiments of the present invention are shown in FIGS. 1 and 2. Each hydrogenation system 100 provides a suitable hydrogenation reactor and a process for separating ethanol from the crude reaction mixture according to an embodiment of the invention. System 100 comprises reaction zone 101 and separation zone 102.

Hydrogen and acetic acid are fed to a vaporizer 103 via lines 104 and 105, respectively, to create a vapor feed stream in line 106 that is directed to reactor 107. In one embodiment, lines 104 and 105 may be combined and jointly fed to the vaporizer 103. The temperature of the vapor feed stream in line 106 is preferably from 100° C. to 350° C., e.g., from 120° C. to 310° C. or from 150° C. to 300° C. Any feed that is not vaporized is removed from vaporizer 103 and may be recycled or discarded. In addition, although line 106 is shown as being directed to the top of reactor 107, line 106 may be directed to the side, upper portion, or bottom of reactor 107.

Reactor 107 contains the catalyst that is used in the hydrogenation of the carboxylic acid, preferably acetic acid. In one embodiment, one or more guard beds (not shown) may be used upstream of the reactor, optionally upstream of the vaporizer, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens.

During the hydrogenation process, a vapor crude ethanol product stream is withdrawn, preferably continuously, from reactor 107 via line 108. According to the present invention, crude ethanol product stream in line 108 remains in the vapor phase. Preferably, vapor crude ethanol product stream has a temperature of from 200° C. to 350° C., e.g., from 250° C. to 350° C. or from 275° C. to 300° C. Optionally, the crude ethanol product stream may be partially cooled by using heat exchangers to reach the operating temperature of the hydrogen separation membrane 130, provided that the crude ethanol product stream remains in the vapor phase. In FIG. 2, membrane 130, the permeating stream 131 comprises hydrogen and trace amounts of other organic vapor. This stream will be re-pressurized and combined with fresh hydrogen before entering vaporizer 103. The retentate stream 132 will comprise all the remaining organic components in the crude ethanol product, plus trace amounts of hydrogen. Since the crude ethanol product is not condensed prior to entering first column 109, the separation system of the invention does not include a knock-out pot or similar device between reactor 107 and first column 109.

For purposes of the present invention, the vapor feed of crude ethanol product stream may provide the majority of the energy needed to drive the separation in the initial separation column 109 (also referred to herein as the "first separation column" or "first column"). Thus, the reboiler installed for first column 109 can be of significantly reduced size, providing equipment cost savings. Due to the reduced energy demand on the reboiler, it preferably operates at a duty that is at least 70%, or at least 78%, less than a comparable reboiler operating on a liquid crude ethanol product fed to the first column at a temperature just below the boiling point thereof.

As shown in FIG. 1, a vapor portion of crude ethanol product stream in line 108 is fed to the side of first column 109. Although various embodiments of the present invention may use different separation systems, it is preferred to withdraw at least one stream comprising acetic acid. In one embodiment, the acetic acid, and any other heavy components, if present, are removed from the vapor crude ethanol product in line 108 and are withdrawn, preferably continuously, as first residue 110. As shown, in some embodiments, energy for the separation step in first column 109 is provided by the heat from the vapor crude ethanol product in line 108 and first column 109 includes a reboiler that operates at reduced duty relative to a comparable system that sends a liquid crude ethanol product at just below the boiling point thereof to first column 109. In some embodiments, under high conversion conditions in the reactor, e.g., greater than 90% or greater than 95%, the acetic may be removed as a dilute acid or weak acid stream that primarily comprises water from the first column 109. First column 109 also forms an overhead vapor that is withdrawn in line 111. This vapor is partially condensed before entering flash vessel 112. Any low boiling-point components and any trace remaining hydrogen can be vented and separated from the process via line 113.

When first column 109 is operated under about 170 kPa, the temperature of the residue exiting in line 110 from column 109 preferably is from 90° C. to 130° C., e.g., from 95° C. to 120° C. or from 100° C. to 115° C. The temperature of the distillate exiting in line 111 from column 109 preferably is from 60° C. to 90° C., e.g., from 65° C. to 85° C. or from 70° C. to 80° C. In some embodiments, the pressure of first column 109 may range from 0.1 kPa to 510 kPa, e.g., from 1 kPa to 475 kPa or from 1 kPa to 375 kPa. Exemplary distillate and residue compositions for first column 109 are provided in Table 2, below. Note that these compositions may change depending on the crude ethanol product composition, acetic acid conversion, the specific operating conditions of the column and whether a majority of the water is removed in the residue. It should also be understood that the distillate and residue may also contain other components, not listed, such as components from the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 2

FIRST COLUMN

|  | Conc. (wt. %) | Conc. (wt. %) | Conc. (wt. %) |
|---|---|---|---|
| Distillate |  |  |  |
| Ethanol | 20 to 95 | 30 to 90 | 30 to 85 |
| Water | 1 to 50 | 2 to 45 | 5 to 40 |
| Acetic Acid | <2 | 0.001 to 0.5 | 0.01 to 0.2 |
| Ethyl Acetate | <70 | 0.1 to 65 | 1 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Other gases | 0.001 to 25 | 0.01 to 20 | 0.1 to 20 |
| Residue |  |  |  |
| Acetic Acid | 0.1 to 70 | 0.1 to 65 | 1 to 55 |
| Water | 35 to 99.9 | 40 to 99.9 | 45 to 99 |
| Ethanol | <2 | <2 | <1.5 |

Preferably, at least 90%, at least 95% or at least 99% of the hydrogen, carbon monoxide, carbon dioxide, methane, and ethane, in combination, that are contained in the crude ethanol product as it exits reactor 107 are yielded from the first column 109 in first distillate 111.

Some species, such as acetals, may decompose in column 109 such that very low amounts, or even no detectable amounts, of acetals remain in the distillate or residue. In addition, an equilibrium reaction between acetic acid and ethanol or between ethyl acetate and water may occur in the crude ethanol product after it exits reactor 107. Depending on the concentration of acetic acid in the crude ethanol product, this equilibrium may be driven toward formation of ethyl acetate. This equilibrium may be regulated using the residence time and/or temperature of crude ethanol product.

As shown, first distillate 111 is cooled and condensed and fed to a flasher 112. Flasher 112 may operate at a temperature of from 50° C. to 500° C., e.g., from 70° C. to 400° C. or from 100° C. to 350° C. The pressure of the flasher 112 may be from 50 kPa to 2000 kPa, e.g., from 75 kPa to 1500 kPa or from 100 kPa to 1000 kPa.

The vapor stream 113 exiting flasher 112 typically will comprise hydrogen and light hydrocarbons such as methane and ethane, as discussed above, and may be purged and/or returned to reaction zone 101. In FIG. 1, vapor stream 113 is combined with the hydrogen feed 104 and co-fed to vaporizer 103. In some embodiments, the returned vapor stream 113 may be compressed before being combined with hydrogen feed 104. In FIG. 2, vapor stream 113 may be purged or returned to reaction zone 101 as desired.

The liquid stream 114 from flasher 112 is withdrawn and preferably refluxed to column 109, for example, at a reflux ratio of from 10:1 to 1:10, e.g., from 3:1 to 1:3 or from 1:2 to 2:1. Lower reflux ratios may increase the amount of ethanol in the first residue depending on the composition of the crude ethanol product. The liquid stream 114 may be further separated to recover ethanol in one or more distillation columns in separation zone 102 as described below. Moreover, over 75% of water from the crude ethanol product was recovered in the residue stream, which minimizes the amount of water in the overhead distillate and reduce the need to remove water from the distillate stream to recover ethanol.

Depending on the water and acetic acid concentration of the residue obtained from first column 109, line 110 may be treated using one or more of the following processes. The following are exemplary processes for further treating first residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from first residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 107. The resulting water stream may be used as an extractive agent or to hydrolyze an ester-containing stream in a hydrolysis unit, or otherwise sent to a waste water treatment facility for disposal.

In other embodiments, for example where residue in line 110 comprises less than 50 wt. % acetic acid, possible options include one or more of: (i) returning a portion of the residue to reactor 107, (ii) neutralizing the acetic acid, (iii) reacting the acetic acid with an alcohol, or (iv) disposing of the residue in a waste water treatment facility. It also may be possible to separate a residue comprising acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue in line 110 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The columns shown in FIGS. 1 and 2 may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section and so on.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention. Further modifications and additional components to reaction zone 101 and separation zone 102 are described below.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

Depending on the intended ethanol application, it may be desirable to remove organics and water from the liquid stream 114. Preferably, a majority of the organics, including ethyl acetate and acetaldehyde, may be removed from liquid stream 114. In some embodiments, removing substantially all of the water produces an anhydrous ethanol product suitable for fuel applications. Water may be removed from the liquid stream 114 using any of several different separation techniques. Particularly preferred techniques include the use of a distillation column, one or more membranes, one or more adsorption units or a combination thereof.

In FIG. 1, liquid stream 114 is introduced to the second column 115, referred to as the "light ends column," preferably in the top part of column, e.g., top half or top third. Second column 115 may be a tray column or packed column. In one embodiment, second column 115 is a tray column having from 5 to 70 trays, e.g., from 15 to 50 trays or from 20 to 45 trays. As one example, when a 30 tray column is utilized in a column without water extraction, line 114 is introduced preferably at tray 2.

Optionally, the light ends column may operate as an extractive distillation column. Suitable extractive agents that may be added to the light ends column include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. In another aspect, the extractive agent may be an aqueous stream comprising water. If the extraction agent comprises water, the water may be obtained from an external source or from an internal return/recycle line from one or more of the other columns, such from the residue of third column 118 (discussed below). Generally, the extractive agent is fed above the entry point of liquid stream 114. When extractive agents are used, a suitable recovery system, such as a further distillation column, may be used to remove the extractive agent and recycle the extractive agent.

Although the temperature and pressure of second column 115 may vary, when at about 20 kPa to 70 kPa, the temperature of the second residue exiting in line 117 preferably is from 30° C. to 75° C., e.g., from 35° C. to 70° C. or from 40° C. to 65° C. The temperature of the second distillate exiting in line 116 preferably is from 20° C. to 55° C., e.g., from 25° C. to 50° C. or from 30° C. to 45° C. Second column 115 may operate at a reduced pressure, near or at vacuum conditions, to further favor separation of ethyl acetate and ethanol. In other embodiments, the pressure of second column 115 may range from 0.1 kPa to 510 kPa, e.g., from 1 kPa to 475 kPa or from 1 kPa to 375 kPa. Exemplary components for the distillate and residue compositions for the second column 115 are provided in Table 3, below. It should be understood that the distillate and residue may also contain other components, not listed, such as components derived from the feed.

TABLE 3

SECOND COLUMN

|  | Conc. (wt. %) | Conc. (wt. %) | Conc. (wt. %) |
|---|---|---|---|
| Second Distillate |  |  |  |
| Ethyl Acetate | 1 to 90 | 2 to 90 | 3 to 80 |
| Acetaldehyde | 0.011 to 30 | 0.01 to 25 | 0.1 to 20 |
| Water | 0.1 to 20 | 0.5 to 15 | 1 to 10 |
| Ethanol | 5 to 90 | 10 to 90 | 15 to 85 |
| Acetal | <15 | 0.001 to 15 | 0.01 to 10 |
| Second Residue |  |  |  |
| Water | 2 to 40 | 5 to 35 | 10 to 30 |
| Ethanol | 60 to 100 | 65 to 95 | 70 to 90 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 2:1, e.g., at least 5:1, at least 8:1, at least 10:1 or at least 15:1. The weight ratio of ethyl acetate in the second residue to ethyl acetate in the second distillate preferably is less than 0.7:1, e.g., less than 0.2:1 or less than 0.1:1. It should be understood that when an extractive agent is used, that the composition of the residue would also include the extractive agent.

Second residue in line 117 may be directed to a third column 118, also referred to as an ethanol product column, to remove water in a third residue 120 from the ethanol product in third distillate 119. Second residue in line 117 may be introduced into the lower part of third column 118, e.g., lower half or lower third. Ethanol product column 118 is preferably a tray column as described above and preferably operates at atmospheric pressure. The temperature of the ethanol distillate exiting in line 119 preferably is from 60° C. to 110° C., e.g., from 70° C. to 100° C. or from 75° C. to 95° C. The temperature of the second residue 120 preferably is from 70° C. to 115° C., e.g., from 80° C. to 110° C. or from 85° C. to 105° C., when the column is operated at atmospheric pressure. Exemplary compositions for the third distillate 119 and third residue 120 are provided below in Table 4. It should be understood that the third distillate and the third residue may also contain other components, not listed, such as components derived from the feed.

TABLE 4

THIRD COLUMN

|  | Conc. (wt. %) | Conc. (wt. %) | Conc. (wt. %) |
|---|---|---|---|
| Third Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Third Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Further purification of third distillate in line 119 to remove any additional water may be performed as necessary. In some embodiments, removing substantially all of the water produces an anhydrous ethanol product suitable for fuel applications. Water may be removed from the distillate in the third distillate in line 119 using any of several different separation techniques. Particularly preferred techniques include the use of a distillation column, one or more membranes, one or more adsorption units or a combination thereof.

Any of the compounds that are carried through the distillation process from the feed or crude reaction product generally remain in the third distillate in amounts of less than 0.1 wt. %, based on the total weight of the third distillate composition, e.g., less than 0.05 wt. % or less than 0.02 wt. %. In preferred embodiments, the finished ethanol composition from distillate 119 is substantially free of acetaldehyde and may comprise less than 8 wppm of acetaldehyde, e.g., less than 5 wppm or less than 1 wppm.

The second distillate in line 116 preferably is refluxed as shown in FIG. 1, for example, at a reflux ratio of from 1:30 to 30:1, e.g., from 1:5 to 5:1 or from 1:3 to 3:1. In some embodiments, the second distillate in line 116 or a portion thereof may be returned reactor 107. For example, it may be advantageous to return a portion of second distillate 116 to reactor 107. The ethyl acetate and/or acetaldehyde in the second distillate may be further reacted in hydrogenation reactor or in a secondary reactor. In certain embodiments, the second distillate may be fed to an acetaldehyde removal column (not shown) to recover acetaldehyde that may be recycled to reactor 107 and purge ethyl acetate from system 100. In other embodiments, the second distillate may be hydrolyzed or fed to an hydrogenolysis reactor (not shown) to produce ethanol from ethyl acetate. In still other embodiments, the second distillate may be purged from system.

In a preferred embodiment of the present invention, as shown in FIG. 2, there is provided one or more membranes for removing at least one non-condensable gas, in particular hydrogen, from crude ethanol product. Higher concentrations of hydrogen in the crude ethanol product, due to excess amounts of hydrogen in reactor 103, may impair the vapor liquid equilibrium in first column 109. In FIG. 2, crude ethanol product 108 from reactor 103 is fed to a membrane 130. Membrane 130 may be a single membrane or an array of membranes for removing at least one non-condensable gas from crude ethanol product 108. In one embodiment, membrane 130 is a palladium-based membrane. Preferably, membrane 130 removes hydrogen from crude ethanol product as permeate stream 131, and yields a crude ethanol product as retentate stream 132. Permeate stream 131 comprises unreacted hydrogen and may be directly or indirectly returned to the reactor 107. Retentate stream 132 is in the vapor phase and is directly fed to first column 109. In one embodiment, retentate stream 132 contains a portion of the heat from reactor 107. The heat in retentate stream 132 may be used as an energy source to drive the separation step in column 109 to yield a residue 110 and a distillate 111 as described above.

The finished ethanol product may be an industrial grade ethanol preferably comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 5.

TABLE 5

FINISHED ETHANOL

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm. In one embodiment, the finished ethanol composition is substantially free of halogen impurities, optionally comprising less than 500 wppb halogen impurities, e.g., less than 100 wppb or less than 50 wppb.

In some embodiments, when further water separation is used, the ethanol product may be withdrawn as a stream from the water separation unit as discussed above. Third distillate 119 may be further purified to form an anhydrous ethanol product stream, i.e., "finished anhydrous ethanol," using one or more additional separation systems, such as, for example, distillation columns (e.g., a finishing column), membranes, adsorption units, or molecular sieves. Anhydrous ethanol may be suitable for fuel applications. In such embodiments, the ethanol concentration of the ethanol product may be higher than indicated in Table 5, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

EXAMPLES

The following examples were prepared with ASPEN Plus 7.1 simulation software to test various feed composition and separation systems.

Example 1

A comparative analysis has been conducted for crude ethanol product produced by hydrogenation with high conversion of acetic acid, e.g., from 99%. Run A was condensed and fed as a liquid to distillation column using a reflux ratio of 2:1. In accordance with embodiments of the present invention, Runs B and C were fed to distillation in vapor form. Hydrogen was removed from Runs B and C using a palladium-based membrane. Run B used a reflux ratio of 2:1, while Run C used a reflux ratio of 1.7:1. As shown in Table 6, feeding the crude ethanol product to the distillation column in the vapor form requires significantly lower than feeding the crude ethanol product in the liquid form. In addition, changing the reflux ratio from 2:1 to 1.7:1 also reduce the amount of energy necessary to separate the components.

TABLE 6

High Conversion of Acetic Acid (99%)

|  | Run A | Run B | Run C |
|---|---|---|---|
| Distillate-wt. % | | | |
| Ethanol | 56.9 | 82.4 | 83 |
| Water | 38 | 10.3 | 9.6 |
| Ethyl Acetate | 2.0 | 2.9 | 3 |
| Acetic Acid | 0.1 | <0.01 | <0.01 |
| Temperature | 92° C. | 89° C. | 89° C. |
| Residue-wt. % | | | |
| Water | 39.9 | 96.9 | 96.9 |
| Acetic Acid | 60.1 | 3.1 | 3.1 |
| Ethanol | <0.01 | <0.01 | <0.01 |
| Temperature | 120° C. | 121° C. | 109° C. |
| % of Water in Residue | 2% | 81.6% | 82.9% |
| Reflux Ratio | 2:1 | 2:1 | 1.7:1 |
| Energy (MMBtu/ton ETOH) | 6.79 | 0.94 | 0.57 |

Example 2

A similar comparative analysis has been conducted for crude ethanol product produced by hydrogenation with conversion of acetic acid of 90%. Run D was condensed and fed as a liquid to distillation column using a reflux ratio of 2:1. In accordance with embodiments of the present invention, Runs E and F were fed to distillation in vapor form, with hydrogen being removed prior to distillation. As shown in Table 7, feeding the crude ethanol product to the distillation column in the vapor form requires significantly lower than feeding the crude ethanol product in the liquid form.

TABLE 7

High Conversion of Acetic Acid (90%)

|  | Run D | Run E | Run F |
|---|---|---|---|
| Distillate-wt. % | | | |
| Ethanol | 36.1 | 46.4 | 48.9 |
| Water | 33.4 | 15.7 | 11.3 |
| Ethyl Acetate | 28.9 | 37.1 | 39.1 |
| Acetic Acid | 1.0 | <0.01 | <0.01 |
| Temperature | 87° C. | 87° C. | 87° C. |
| Residue-wt. % | | | |
| Water | 9.2 | 66.7 | 70.2 |
| Acetic Acid | 90.1 | 33.3 | 29.8 |
| Ethanol | <0.01 | <0.01 | <0.01 |
| Temperature | 122° C. | 122° C. | 122° C. |
| % of Water in Residue | 3% | 65% | 76% |
| Reflux Ratio | 2:1 | 2:1 | 1.8:1 |
| Energy (MMBtu/ton ETOH) | 9.2 | 1.94 | 0.95 |

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
   hydrogenating acetic acid from an acetic acid feed stream in a reactor to produce a vapor crude ethanol product;
   separating the vapor crude ethanol product with a membrane into a permeate stream comprising at least one non-condensable gas and a retentate stream, wherein the retentate stream comprises acetic acid and ethanol;
   separating at least a portion of the retentate stream in a first distillation column to produce a first residue comprising acetic acid and a first distillate comprising ethanol and the at least one non-condensable gas; and
   recovering ethanol from the first distillate.

2. The process of claim 1, wherein the at least one non-condensable gas is selected from the group consisting of hydrogen, carbon monoxide, carbon dioxide, ethane, methane, and mixtures thereof.

3. The process of claim 1, wherein the retentate stream is not condensed prior to entering the first distillation column.

4. The process of claim 1, further comprising separating at least a portion of the first distillate in a second distillation column into a second residue comprising ethanol and water, and a second distillate comprising ethyl acetate.

5. The process of claim 4, further comprising returning a portion of the second distillate to the reactor.

6. The process of claim 4, further comprising separating at least a portion of the second residue in a third distillation column into a third distillate comprising ethanol and a third residue comprising water.

7. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

8. A process for producing ethanol, comprising the steps of:
   providing a vapor crude ethanol product comprising ethanol, acetic acid, water, ethyl acetate, and at least one non-condensable gas;
   separating the vapor crude ethanol product with a membrane into a permeate stream comprising at least one non-condensable gas and a retentate stream, wherein the retentate stream comprises acetic acid and ethanol;
   separating at least a portion of the retentate stream in a first distillation column into a first residue comprising acetic acid and a first distillate comprising ethanol and the at least one non-condensable gas;
   separating at least a portion of the first distillate to yield a vapor stream comprising the at least one non-condensable gas and a liquid stream comprising ethanol; and
   recovering ethanol from the liquid stream.

9. The process of claim 8, further comprising separating at least a portion of the liquid stream in a second distillation column into a second distillate comprising ethyl acetate and a second residue comprising ethanol.

10. The process of claim 9, further comprising separating at least a portion of the second residue in a third distillation column into a third distillate comprising ethanol and a third residue comprising water.

11. A process for producing ethanol, comprising the steps of:
- hydrogenating acetic acid from an acetic acid feed stream in a reactor to produce a vapor crude ethanol product;
- separating at least a portion of the vapor crude ethanol product in a first membrane to produce a first permeate comprising at least one non-condensable gas, and a first retentate comprising acetic acid, ethanol, ethyl acetate and water; and
- recovering ethanol from the first retentate,
- wherein the at least one non-condensable gas is selected from the group consisting of hydrogen, carbon monoxide, carbon dioxide, ethane, methane, and mixtures thereof.

12. The process of claim 11, further comprising the steps of adding the first retentate in vapor form to a first distillation column and separating at least a portion of the first retentate in the first distillation column into a first distillate comprising ethanol and ethyl acetate, and a first residue comprising acetic acid and water.

13. The process of claim 12, further comprising separating at least a portion of the first distillate in a second membrane to produce a second permeate comprising at least one non-condensable gas, and a second retentate comprising ethanol and ethyl acetate.

14. The process of claim 12, further comprising separating at least a portion of the first distillate in a second column to produce a second residue comprising ethanol and a second distillate comprising ethyl acetate.

15. The process of claim 1, further comprising returning at least a portion of the permeate stream to the reactor.

16. The process of claim 8, wherein the at least one non-condensable gas is selected from the group consisting of hydrogen, carbon monoxide, carbon dioxide, ethane, methane, and mixtures thereof.

17. The process of claim 8, further comprising returning at least a portion of the permeate to the reactor.

18. The process of claim 11, further comprising returning at least a portion of the first permeate to the reactor.

* * * * *